United States Patent [19]
Redler et al.

[11] Patent Number: 4,575,634
[45] Date of Patent: Mar. 11, 1986

[54] ASSAYING COMPOSITE STRUCTURES

[75] Inventors: Elisa Redler; Gerald Entine, both of Waban, Mass.

[73] Assignee: Radiation Monitoring Devices, Inc., Watertown, Mass.

[21] Appl. No.: 433,276

[22] Filed: Oct. 7, 1982

Related U.S. Application Data

[63] Continuation-in-part of Ser. No. 336,183, Dec. 31, 1981, abandoned.

[51] Int. Cl.$^4$ ............................................. G01N 23/09
[52] U.S. Cl. ................................. 250/358.1; 250/391
[58] Field of Search ................ 250/358.1, 359.1, 392, 250/391, 390; 378/53, 88

[56] References Cited

FOREIGN PATENT DOCUMENTS 1389838 4/1975 United Kingdom .

OTHER PUBLICATIONS

Eichholz et al., *Radiochem. Radioanal. Letters* 19/3/157–161/1974 "Determination of Boron and Cadmium by Neutron Absorption".
Vegvari, et al., *Chem. Ab.* 90/214/1979 "Determination of the Boron Content of Glasses by Neutron Absorption".
Hoefer, et al., *Chem. Ab.* 82/28/1975 "Non-Destructive Determination of Glass Content and of Voids in Reinforced Plastics".
Cesareo, et al., *Int. Jnal. of Appl. Radiation and Isotopes*, vol. 30, No. 10 (Oct. 1979) pp. 589–594 "Non-Destructive Analysis of Silver Alloys by Means of Low Energy Gamma-Rays and Neutron Transmission Measurements".
Sinclair, et al., *Materials Evaluation*, 56–60, (Mar. 1975) "Scintillography Using Thermal Neutrons".

*Primary Examiner*—Janice A. Howell
*Assistant Examiner*—Constantine Hannaher

[57] ABSTRACT

Measurement of the amount of a constituent such as glass in a composite structure, by passing neutrons or gamma rays through the structure and measuring the degree to which the neutrons or gamma rays are absorbed.

23 Claims, 9 Drawing Figures

ASSAYING COMPOSITE STRUCTURES

BACKGROUND OF THE INVENTION

This application is a continuation-in-part of our co-pending application Ser. No. 336,183, filed Dec. 31, 1981, now abandoned.

This invention relates to measuring the amount of glass and other constituents of composite structures. It is often desirable, for example, to measure the glass content of glass-reinforced plastics.

SUMMARY OF THE INVENTION

In a first aspect, the invention features a fast, accurate, and relatively inexpensive measurement of the amount of glass in a composite structure, by passing neutrons through the structure and measuring the degree to which the neutrons are absorbed in boron contained in the glass. In preferred embodiments, the boron is the isotope $_5B^{10}$; there is the further step of providing relative movement between the material and the source so as to measure the amount of glass at a plurality of locations; the relative movement is a scanning movement to measure the spatial distribution of glass in the structure; the neutrons have the energy level of thermal neutrons; and the degree of neutron absorption is averaged over a period of time.

In a second aspect, gamma rays are used in place of neutrons. In preferred embodiments, the material comprises an organic resin; the constituent is selected from the group consisting of flame retardant compounds (containing bromine, antimony, titanium, or chlorine), mica, calcium carbonate, glass, talc, or aluminum trioxide; a neutron absorption is also measured for the same sample, to allow measurement of the amounts of two ingredients, one absorptive of both gamma rays and neutrons and the other absorptive of gamma rays only; the constituent being measured comprises an element of atomic number larger than the atomic number of any other element found in the composite material in other than negligible amounts, to assure that gamma ray absorption in the material is influenced predominantly by the constituent being measured; for glass and organic resin, no other constituent has an element of atomic number greater than 11; gamma rays of two different energies are passed through the composite material; the higher energy gamma ray is used to measure the geometry or total mass along the path separating the source and detector, the lower energy gamma ray to make a measurement sensitive both to the geometry or total mass and to the amount of said constituent, and the ratio between the two measurements to determine the amount of the constituent.

In a third aspect, apparatus is provided for assaying the amount of an ingredient in a composite material, the apparatus comprising means for directing a beam of neutrons or gamma rays or both at said material, means for detecting the intensity of the beam after it emerges from said material, and means for determining the amount of said ingredient from a specified relationship. In preferred embodiments, the beam is neutrons and the neutron source comprises a neutron source, a surrounding paraffin moderator, and a protective outer casing; the neutron detector comprises a He$^3$ detector wrapped partially in a boron rubber material such as Boraflex; a sample holder is provided for sliding the sample into and out of the path between the source of neutrons or gamma rays and the detector thereof; there are provided a computer processor, memory, and software therefor.

In a fourth aspect, provisions are made for maintaining the same volume and the same weight of material for both the calibrations and the test sample so as to provide a determination of the amount of ingredient in the test sample in terms of percentage weight. In preferred embodiments, the material being assayed is pellets and the weight and volume of the samples being assayed is kept the same as for the calibration samples by placing the same weight of pellets in a sample holder as used in the calibrations and then shaking, stirring, or packing the pellets into the same volume as used in the calibration; there is provided the step of measuring the weight of the calibration samples and the test sample and correcting the result calculated by said relationship so that the result is indicative of the percentage by weight of said ingredient in the test sample.

In another aspect the measurement is made in a continuous production environment. In preferred embodiments the result of the measurement is used to control the amount of an ingredient used in the production of the composite.

The invention provides a practical technique for detecting variation in glass content of sheet as well as pelletized materials. Automobile body parts, such as fenders, can be relatively rapidly scanned for flaws, areas where abnormal glass content is present, and sample-to-sample variations from the mean can be checked for unacceptable variance.

Other advantages and features of the invention will be apparent from the following description of the preferred embodiments thereof and from the claims.

DESCRIPTION OF THE PREFERRED EMBODIMENTS

We turn now to a description of the preferred embodiments.

Figure 1:
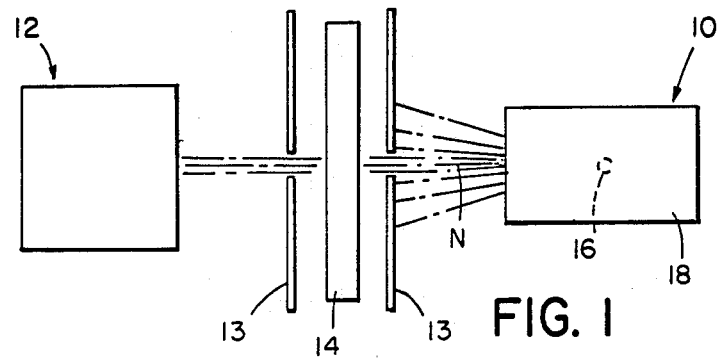
FIG. 1 is a diagrammatic view of a first said preferred embodiment.
Figure 2:
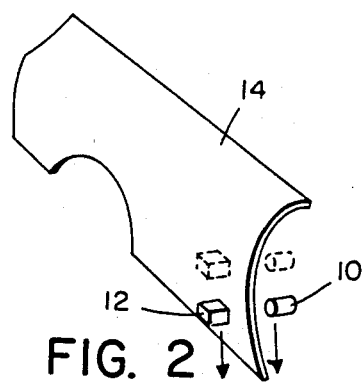
FIG. 2 is a diagrammatic view of said embodiment being used to scan a glass-reinforced composite automobile body part for flaws.
Figure 3:
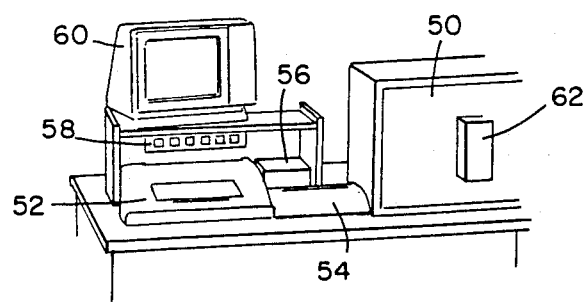
FIG. 3 is a perspective view of another embodiment, the one presently most preferred.
Figure 4:
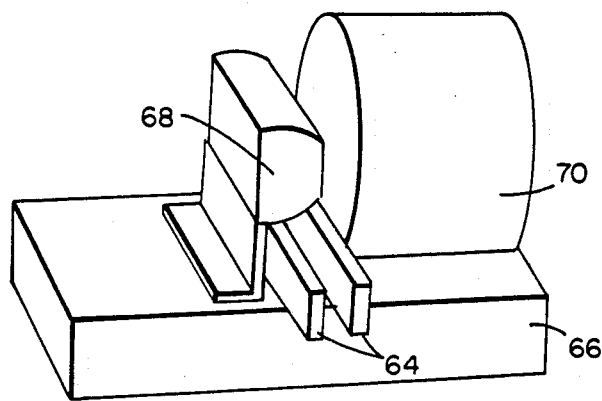
FIG. 4 is a somewhat diagrammatic perspective view of an interior portion of the measuring unit of said embodiment.
Figure 5:
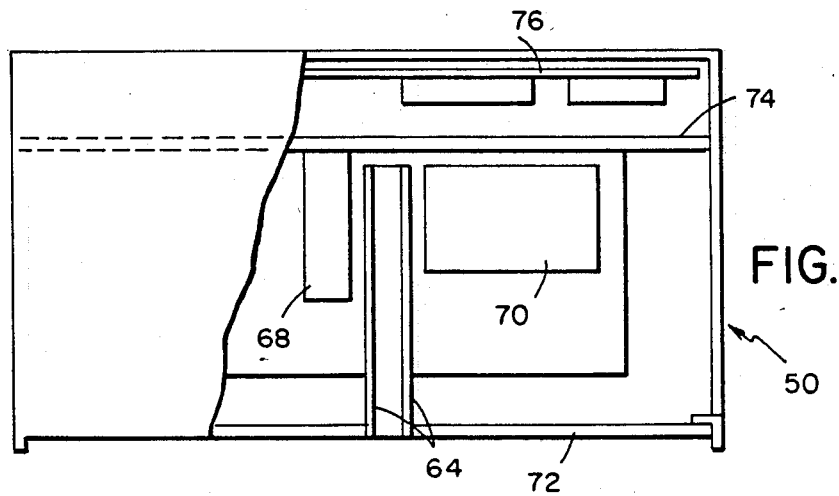
FIG. 5 is a somewhat diagrammatic plan view, partially cut away to expose the interior, of the measuring unit.
Figure 6:
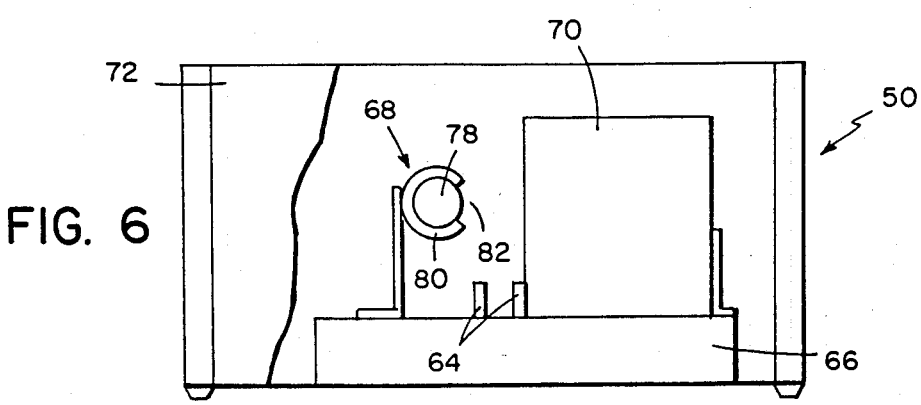
FIG. 6 is a somewhat diagrammatic front elevation view, also partially cut away, of the measuring unit.

Turning first to the embodiment shown in FIGS. 1 and 2, there is shown in FIG. 1 neutron source 10, neutron detector 12, and composite structure 14 containing glass, organic resins, and other components. Apertured neutron absorbing boron containing sheets 13 collimate the neutron beam. Some of neutrons N travelling from the source to the detector through composite 14 are absorbed by $_5B^{10}$ atoms present in the glass of the composite. This boron isotope is an excellent absorber of thermal neutrons. Most other elements of glass and composites have very low neutron absorption.

Neutron source 10 consists of a 54 microCurie source 16 of Californium 252 embedded in a cylindrical paraffin moderator 18. High energy neutrons emitted by the Californium source are moderated with paraffin, so that thermal (or low energy) neutrons are emitted by source 10. The source and detector are typically separated by a 1 to 6 inch gap. Detector 12 is a helium-3 proportional counter.

In use, the composite structure can be moved relative to the source and detector in a scanning movement, as suggested in FIG. 2, so as to measure the spatial distribution of glass within the composite. Such scanning movements could be used to check for flaws, where an improper percentage of glass is present.

Turning next to the second and presently most preferred embodiment, there is shown in FIGS. 3-6, a measuring unit 50, microprocessor 52 (an Apple II plus microcomputer), printer 54, control switches 58, and CRT display 60. Measuring unit 50 has sliding sample holder 62 (a rectangular parallelepiped chamber open at the top for receiving a sample), which slides horizontally inward from the front of the unit on tracks 64. Inside the unit, mounted with tracks 64 on a chassis 66, are neutron detector 68 and neutron source 70. Tamper-proof screws secure chassis 66, front panel 72, and a rear inside panel 74. Behind rear panel 74 there is installed printed circuit board 76 and power supplies, which can be accessed without removing panel 74. Detector 68 may also be removed through an opening (not shown) in panel 74.

Detector 68 consists of a stainless steel $He^3$ detector 78 (Reuter-Stokes model RS-P4-1606-215, with rolled aluminum covering) surrounded by a neutron-absorbing Boraflex outer covering 80 (Bisco Corp., 0.04 gm/cm$^2$ B10) except at opening 82, directed toward the neutron source and the sample.

Neutron source 70 consists of a 54 microCurie source of Californium 252 (Amersham Corp., C64544 (ANSI), SFC (7)(IAEA) Capsule X.1, code CVN.1) suspended by a stainless steel helix inside a paraffin moderator, all inside a cylindrical aluminum can (Zero Corp. ZTR-140; 8.75 inch diameter; 6.63 inches long; 0.040 inch wall) sealed with a press-fit aluminum and cap. The aluminum can protects the neutron source and would contain the paraffin in the event of fire.

Sample holder 62 is adapted to hold pellets, which are simply poured in at the top, or to support solid sheet materials, which are secured (e.g., with spring clamps or other means) to a vertical side thereof.

Figure 7:
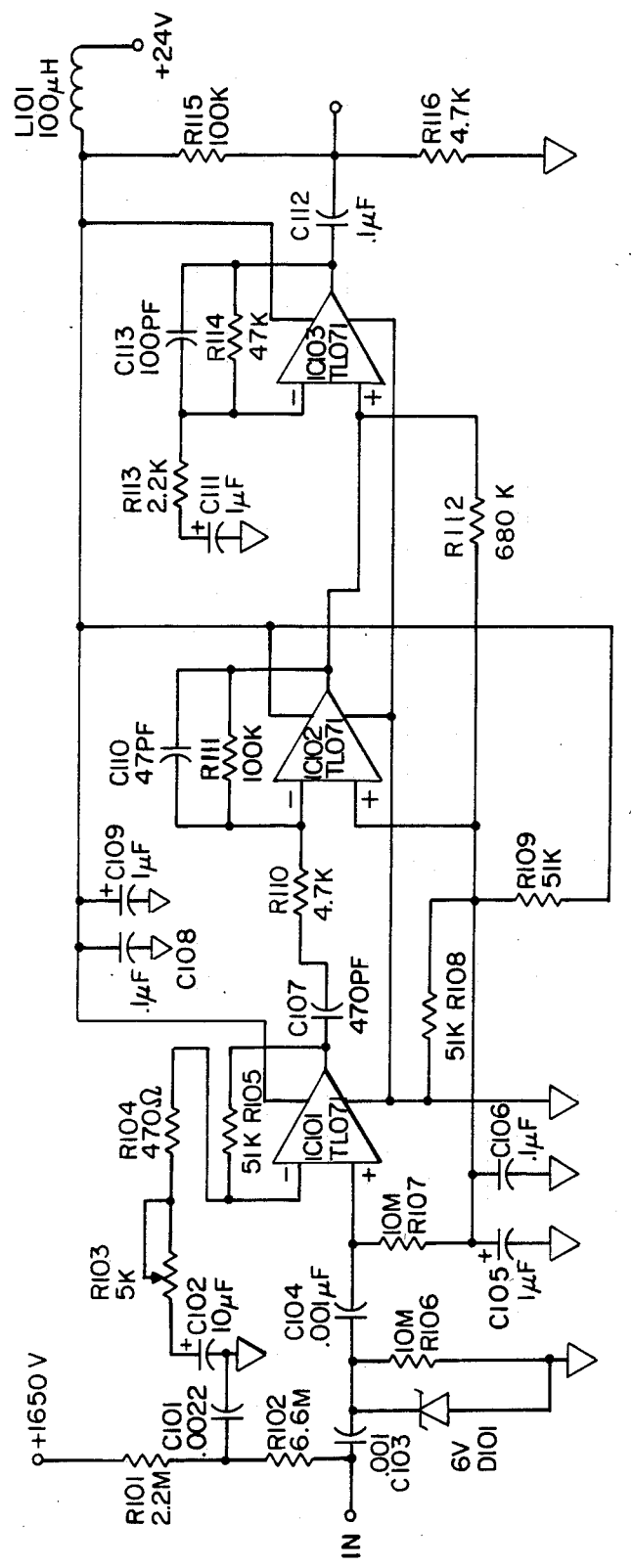
FIGS. 7–9 are schematics of the circuitry of the presently most preferred embodiment.
Figure 8:
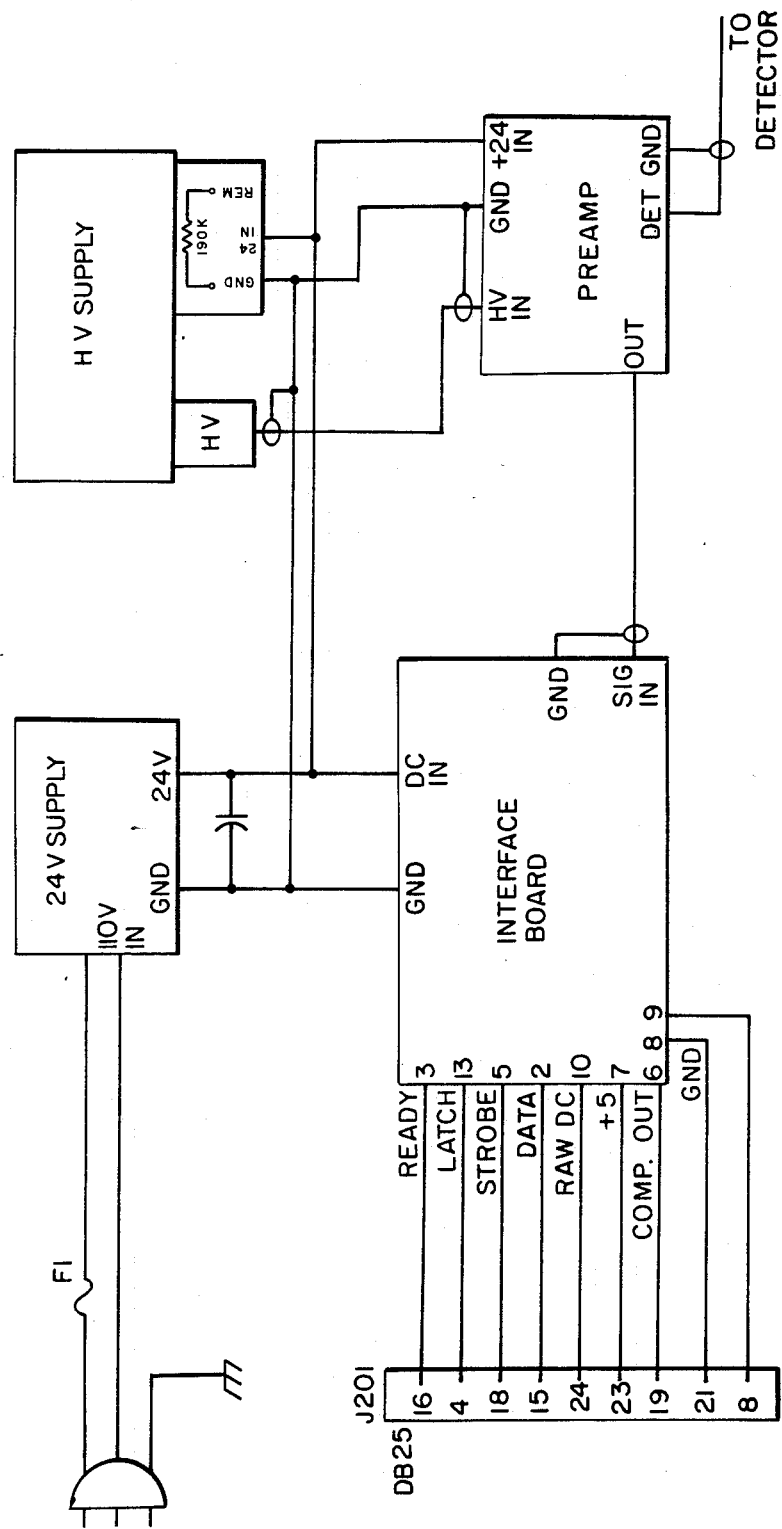
Figure 9:
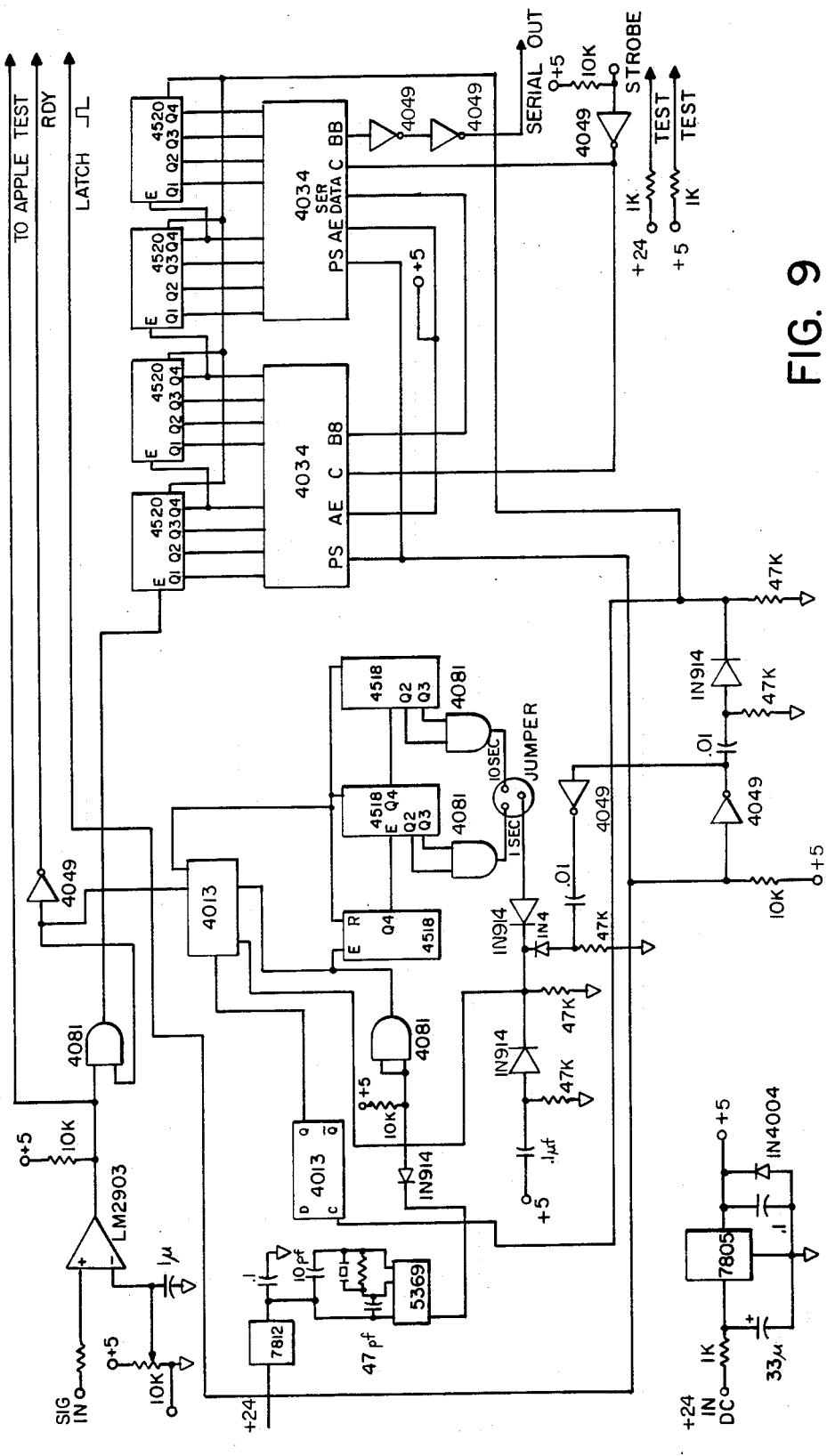

Shown in FIGS. 7-9 are schematics of the circuitry resident in the measuring unit. FIG. 7 shows the pulse amplifier for amplifying the pulses received from the neutron detector. FIG. 8 shows the overall circuitry, including the pulse amplifier (at the lower right), two power supplies, and an interface board. FIG. 9 shows the circuitry of the interface board, which supplies the microcomputer with a total number of neutron detections during each ten second interval of the measurement period. A counter counts the pulses received from the pulse amplifier and transfers the total to a buffer every ten seconds. The microcomputer is supplied with the contents of the buffer at ten second intervals.

To calibrate a measurement for a particular type of composite sample, two measurements are made: a first detector reading $I_{S1}$ is taken with a target identical to the composite to be tested except that it contains somewhat less glass (preferably about 20% less), and a second reading $I_{S2}$ is taken with a target identical to the composite except that it contains somewhat more glass (preferably about 20% more). Naturally the glass content of the composite to be tested is not accurately known in advance and must be estimated from other information as is usually available in most quality control or process control situations.

A background detector reading $I_B$ is taken with a near perfect neutron absorber, such as cadmium or boron, as the target. This reading measures the neutron background signal. Detector readings are in the form of counts per second, representing the frequency of neutron arrivals. The background reading does not change with the different samples and can thus be measured once and built into the computer software.

The relationship between a detector reading $I_S$ (the number of neutrons detected in a fixed time interval) and the amount of glass present in a particular composite structure is given approximately as $$I_S = (I_O - I_B)\exp(-K_G M_G)\exp(-K_R M_R) + I_B$$

where $I_{S1}$, $I_{S2}$, and $I_B$ are as already defined, $I_O$ is the signal with no sample in the beam, $K_G$ is the neutron mass absorption coefficient for glass (most of which arises from the $_5B^{10}$ content), $M_G$ is the mass of the glass per unit area in the beam, $K_R$ is the coefficient of neutron absorption and scatter for the remainder of the composite, i.e., everything but the glass ($K_R$ is much less than $K_G$), and $M_R$ is the mass per unit area of the remainder of the composite.

Since the mass of the composite $M_C$ equals $M_G + M_R$, the above equation becomes $$I_S = (I_O - I_B)\exp(-K_R M_C)\exp(K_R - K_G)M_G + I_B$$

in which the unknown $M_G$ appears in only one term and the other terms are constant for a given type of composite. This formula reduces to a straight line when plotted on semilog paper against the unknown $M_G$. If one does measurements on two known standards of glass content $F_1$ percent and $F_2$ percent and measures $I_{S1}$ and $I_{S2}$, both the slope and the intercept of the line in log space can be calculated and the glass content of the unknown $F_X$ can be shown to be $$F_X = F_1 + \left[(F_2 - F_1) \ln\left(\frac{I_{S2} - I_B}{I_{S1} - I_B}\right)\right] \ln\left(\frac{I_{S1} - I_B}{I_{SX} - I_B}\right)$$

$$F_X = F_1 + G \ln\left(\frac{I_{S1} - I_B}{I_{SX} - I_B}\right)$$

where $I_{SX}$ is the detector reading for the unknown material. This can be rewritten as $$F_X = F_1 + G \ln(I_{S1} - I_B) - G \ln(I_{SX} - I_B)$$

where everything is a constant determined by the calibration measurements except $I_{SX}$ which varies with the unknown. Thus, once a calibration curve is prepared for a particular type of composite, the glass content can be readily determined.

The range over which the calibration curve is valid depends not only on the precision of the measurements of $I_{S1}$ and $I_{S2}$, but also on the assumption that $K_R$, the absorption and scattering coefficients of the nonglass components of the composites, do not change very much due to large changes in the ratio of the nonglass constituents relative to the two calibration standards. This assumption is usually valid since $K_R$ is usually much less than $K_G$ so small changes in the other components do not cause large changes in $K_R$ or neutron transmission relative to the glass signal.

A less exact calibration can be made by (1) using calibration measurements further away than the preferred 20% (nonlinearities may become noticeable, however) or (2) using only one calibration measurement and assuming a slope for the linear (on log paper) relationship spoken of earlier. The latter will work fairly well when the calibration measurement is close to the actual measurement because the slope is fairly similar for many types of samples.

To initiate use of the device, the various units are turned on, and the software is loaded via the disk drive. The program begins by prompting for the date. It is important that this be entered correctly since the program automatically corrects for the half-life of the radioactive source employed to perform the quantitation. Next, the operator's name is entered. The program will then present a list of options: (1) calibration, (2) assay, (3) calibration list, (4) assay list, (5) instructions, or (6) exit program. Before performing an assay a calibration must be entered into the computer memory. To perform the calibration, two specimens of known glass content are required. The calibration mode is chosen by typing an entry on the keyboard. The disk will then load the calibration program, which will first ask for the type of plastic. A selection from a list of nominal times for a given calibration precision must then be made. Next, the weight percentage of glass in the first calibration specimen is entered. The program will then ask that the sample be prepared for calibration. The calibration sample is then inserted into the holder, and the holder is slid into the measuring module, making certain that the holder is flush with the front panel. An entry is made on the keyboard to proceed with the calibration measurement. The time left until the first calibration is completed is indicated in seconds on the monitor. When the first calibration measurement is completed a tone will sound. The weight percentage of the second calibration sample is then entered and the second calibration sample is inserted into the measuring module. A tone indicates that the second calibration has been completed and the calibration precision is posted in percent. The calibration can then be saved in disk memory. Additional calibrations may then be performed.

To begin an actual measurement or assay, the assay mode is chosen using the keyboard, and the program asks for the type of plastic and sample name. A list of times for a given assay precision will then appear, and one must be selected. The precision table that appears has been updated on the basis of the previous calibration measurements. The unknown sample is then placed in the specimen holder, the holder placed in the measuring module, and the assay begun by an entry on the keyboard. A flashing announcement indicates that the assay is in progress, and every ten seconds the time remaining and the glass content and precision are updated. A tone indicates that the assay has been completed, and the glass content and assay precision are displayed. The program then asks if the assay is to be saved. A list of calibrations on file can be obtained by returning to the original list of six options. The calibration file can be deleted or printed.

The device basically measures the percent glass per unit volume rather than per unit weight, which is the value more typically desired. This is because the beam passes through the same area for each measurement. However, it is possible to convert from a volume measure to a weight measure. For particulate material such as the plastic pellets used in the molding industry, a constant weight of pellets is put into the sample holder and the bulk packing density is varied by shaking, stirring, or packing so that the volume occupied by the sample is the same as that occupied by the calibration standards. That can be achieved simply by comparing the height of the pellets to a line on the sample holder (or by using an electric eye at the height of the line), and then shaking to raise the height or tapping the holder on a hard surface to cause closer packing and thus a lower height. In this way each sample has both a constant volume and a constant weight, and percentage glass per unit weight can thereby be measured. This technique will even account for variation in the porosity of the pellets between samples. To help assure that the pellet packing remains uniform between samples (and thus ease the task of shaking or packing to achieve the desired volume), it is best to pour the pellets into the sample holder from a fixed height.

Small corrections for differences in volume or weight can be corrected by linear extrapolation, done manually or with modified software. For sheet material of constant thickness, the use of the two calibration sample technique will result in answers directly in terms of weight percent of glass. Small differences in thickness can also be corrected by linear extrapolation, done manually or with modified software.

For samples of significantly different weight or where extreme precision is required, the mass must be taken into account before the logarithms are taken in the basic calculation. Using manual techniques such as weighing with balances, or automated techniques such as ultrasound or high energy ground transmission, the weight or mass data can be measured and supplied to the computer which performs the calculation.

Another technique for achieving constant weight per unit beam area would be to provide the sides of the holder with accordian like sides that could be gently opened or closed to adjust the height of the pellets until their top surface matches a prescribed line on the holder. This results in a constant amount of sample weight being in the beam path.

OTHER EMBODIMENTS

Other embodiments are within the following claims. For example, the measurement period can be varied (long measurement periods generally give greater accuracy as they permit more averaging of detector readings; typical measurement periods have ranged from 1 second to 1 hour). Other sources and detectors could be used: an electronic neutron source or an american-lithium source could be used; and the detector could be another neutron detector such as $BF_3$ or a LiI(Eu) scintillator crystal with a photo multiplier tube, particularly where size is important. Also the source and detector could be packaged in a portable, battery-powered unit, and electronics could be added to provide a display of the percentage of glass in the structure under test. Neutron absorption could also be measured by measuring alpha particle emission from the absorbing boron.

Assays can also be carried out using gamma rays in place of, or in addition to, neutrons. Gamma rays are absorbed by the silicon in glass, and thus are useful with glasses in which boron is not used. Gamma rays are also absorbed by many other additives used in composites, e.g., flame retardants (which typically include bromine, antimony, titanium, or chlorine), mica, calcium carbonate, aluminum trioxide, and talc.

When using gamma rays, it is preferred that all other elements of the composite (additives and base material) have atomic numbers substantially lower than that of the additive to be assayed. This is, for example, true in a glass and plastic composite, because silicon (atomic number 14) has an atomic number far in excess of that of oxygen (atomic number 8), the element with the next highest atomic number. But if aluminum trioxide were added to the composite, absorption by the aluminum (atomic number 13) would interfere with absorption by the silicon. It is thus preferred in the case of assaying glass that there not be in the composite (except in amounts negligible compared to the glass) any elements with atomic numbers above 11.

Gamma rays can also be used in conjunction with neutrons. Such a two-beam approach is especially useful in the situation just described of assaying a composite containing both glass and another additive with an element close in atomic number to silicon. In that situation, the neutron measurement gives the amount of glass, and the gamma ray measurement the combined amount of glass and the other additive. The amount of the other additive can then be calculated from the difference between the two measurements.

Using gamma rays of two different energies, one can also provide a measurement that is independent of the geometry of the sample (e.g., independent of the packing density of pellets) or of the measurement (e.g., independent of the spacing between source and detector, such as could be the case in a scan of a manufactured article). For example, a low KeV measurement (which requires that the sample be free of heavy elements such as lead) would provide a measurement sensitive to glass content and geometry, and a high KeV measurement would provide one sensitive to geometry only. The ratio of the two would thus provide a measurement of glass content.

The presently preferred embodiment using gamma rays has two 100 microCurie cadmium 109 sources, which give off gamma rays at two energies, and a cadmium-telluride solid-state, gamma ray detector (Radiation Monitoring Devices, Inc., Model A101B4). The sources are mounted in the vicinity of the neutron detector and the detector in the vicinity of the neutron source, so that the beam is in line with the neutron beam but oppositely directed. The two sources are used to widen the target area of the gamma-ray beam to approximately that of the neutron beam.

Advantages of gamma rays are that they provide a larger output signal than neutrons and that higher source intensities can be used (because it is easier to shield gamma rays), all of which provides greater precision.

Another embodiment is to use the described neutron or gamma-ray measurements in a process control environment, to continually assay the output of a manufacturing process. For example, in the production of composites in pellet form, arrangements could be made to periodically fill a cavity with pellets and to direct the neutron or gamma ray beam across the cavity. This would permit a nearly real time measurement, for example, of the glass content of a glass-plastic composite. Measured variation from a desired percentage could be used to automatically control the amount of glass being added to the composite. In this case the computer is not essential since it is sufficient for the electronics to compare the averaged detector signal directly to a reference level set when the line is running normally, and to use the difference between the detector and reference signals to control the amount of glass used in the composite.

Other embodiments include comparison detectors for inspecting, for example, helicopter blades and tank armor. With helicopter blades, a tiny source could be inserted into the blade interior and a detector run across the outer surface. The two-energy gamma ray technique described above would be particularly useful here because of the variation in separation between source and detector. Instead of measuring the absolute glass content of the blade, a comparison would be made between desired and actual plots of the spatial distribution of glass content, the plots being generated as the detector is run across the blade surface.

What is claimed is:

1. The method of measuring the glass content of a glass-containing composite material, comprising the steps of exposing said material to a source of neutrons, measuring the degree of neutron absorption by boron contained in said glass, and determining said glass content on the basis of said degree of neutron absorption.

2. The method of claim 1 wherein said boron is the isotope $_5B^{10}$.

3. The method of claim 1 wherein said measuring step comprises detecting the number of neutrons from said source that pass through said material after impinging thereupon.

4. The method of claim 1 further comprising the step of providing relative movement between said material and said source so as to measure the amount of said glass at a plurality of locations.

5. The method of claim 4 wherein said relative movement is a scanning movement so as to measure the spatial distribution of said glass in said structure.

6. The method of claim 5 wherein said spatial distribution is compared to a desired spatial distribution to find flaws in said composite.

7. The method of claim 1 wherein said neutrons have the energy level of thermal neutrons.

8. The method of claim 1 wherein said measuring the degree of neutron absorption is averaged over a period of time.

9. The method of claim 1 wherein said material comprises an organic resin.

10. The method of claim 1 wherein said measurement is made at intervals of a composite material at a stage during its continuous production.

11. The method of claim 10 wherein said measurement is used to alter the amount of said constituent used in said production.

12. The method of claim 1 wherein said measuring step further comprises detecting the intensity of a beam of neutrons after it emerges from said material, and wherein said determining step is based on the relationship $$F_X = F_1 + \left[(F_2 - F_1) \ln\left(\frac{I_{S2} - I_B}{I_{S1} - I_B}\right)\right] \ln\left(\frac{I_{S1} - I_B}{I_{SX} - I_B}\right)$$

where $I_B$ is the background intensity observed when a perfect absorber replaces said material, $I_{S1}$ is the intensity observed for a first calibration sample, $I_{S2}$ is the intensity observed for a second calibration sample, $F_1$ is the amount of glass in said first calibration sample, $F_2$ is the amount of glass in said second calibration sample, and $F_X$ is the amount of glass in said material.

13. The method of claim 1 further comprising the step of maintaining the same volume and the same weight of material for both the calibrations and the test sample so as to provide a determination of the amount of glass in the test sample in terms of percentage by weight.

14. The method of claim 13 wherein the material being assayed is pellets and the weight and volume of the samples being assayed is kept the same as for the calibration holder as used in the calibrations and then shaking, stirring, or packing the pellets into the same volume as used in the calibration.

15. The method of claim 1 further comprising the step of measuring the weight of the calibration samples and the test samples and correcting the result calculated by said relationship so that the result is indicative of the percentage by weight of glass in the test sample.

16. The method of claim 1 wherein said exposing step comprises exposing said material to a source of neutrons that has a surrounding paraffin moderator and a protective outer coating.

17. The method of claim 1 wherein said measuring step comprises detecting the intensity of neutrons using a $He^3$ detector wrapped partially in a boron rubber matieral.

18. The method of claim 1 wherein said determining step comprises using a computer and software to determine said glass content.

19. The method of claim 1 further comprising the steps of
exposing said material to a source of gamma rays,
measuring the degree of gamma-ray absorption to make a measurement sensitive to the geometry or total mass, and
comparing the neutron and gamma-ray measurements to determine the amount of glass.

20. The method of assaying a composite material to determine the amount of two constituents therein comprising
exposing said material to a source of gamma rays,
exposing said material to a source of neutrons,
measuring the degree of gamma-ray absorption by said material,
measuring the degree of neutron absorption by said material,
said material comprising two constituents, one absorptive of both gamma rays and neutrons and the other absorptive of gamma rays only,
one said constituent being measured comprising an element of atomic number larger than the atomic number of any other element found in said composite material in other than negligible amounts, to thereby assure that gamma ray absorption in said material is influenced predominantly by said constituent with a larger atomic number, and
determining the amount of both constituents based on both absorption measurements.

21. The method of claim 20 wherein said constituent is glass and said composite material consists of glass and organic resin and no other constituent with an element of atomic number greater than 11.

22. The method of assaying the amount of a constituent in a composite material comprising the steps of
directing a beam of neutrons or gamma rays or both at said material,
detecting the intensity of the beam after it emerges from said material,
determining the amount of said constituent from the relationship $$F_X = F_1 + \left[ (F_2 - F_1) \ln\left(\frac{I_{S2} - I_B}{I_{S1} - I_B}\right) \right] \ln\left(\frac{I_{S1} - I_B}{I_{SX} - I_B}\right)$$

where $I_B$ is the background intensity observed when a perfect absorber replaces said material, $I_{S1}$ is the intensity observed for a first calibration sample, $I_{S2}$ is the intensity observed for a second calibration sample, $F_1$ is the amount of said constituent in said first calibration sample, $F_2$ is the amount of said constituent in said second calibration sample, and $F_X$ is the amount of said constituent in said composite material being assayed,
maintaining the same volume and the same weight of material for both the calibrations and the test sample so as to provide a determination of the amount of said consituent in the test sample in terms of percentage by weight,
wherein the material being assayed is pellets and the weight and volume of the samples being assayed is kept the same as for the calibration samples by placing the same weight of pellets in a sample holder as used in the calibrations and then shaking, stirring, or packing the pellets into the same volume as used in the calibration.

23. The method of claim 22 further comprising the step of measuring the weight of the calibration samples and the test samples and correcting the result calculated by said relationship so that the result is indicative of the percentage by weight of said ingredient in the test sample.

* * * * *